United States Patent [19]

Parkin

[11] Patent Number: 4,747,719

[45] Date of Patent: May 31, 1988

[54] SWAB APPLICATOR

[76] Inventor: Cole Parkin, 1727 Saint Ann St., Jackson, Miss. 39202

[21] Appl. No.: 889,634

[22] Filed: Jul. 28, 1986

[51] Int. Cl.⁴ .................. A61M 35/00; A47L 13/17
[52] U.S. Cl. .................................. 401/132; 401/134; 401/196; 604/1; 604/3
[58] Field of Search ............ 401/132, 196, 133, 134; 604/1, 2, 3

[56] References Cited

U.S. PATENT DOCUMENTS

| | | | |
|---|---|---|---|
| 3,411,853 | 11/1968 | Hoff | 401/134 |
| 3,482,920 | 12/1969 | Schwartzman | 401/132 |
| 3,640,268 | 2/1972 | Davis | 604/1 X |
| 3,773,035 | 11/1973 | Aronoff et al. | 604/1 X |
| 3,792,699 | 2/1974 | Tobin et al. | 401/133 X |
| 4,014,746 | 3/1977 | Greenspan | 604/1 X |

FOREIGN PATENT DOCUMENTS

| | | | |
|---|---|---|---|
| 471225 | 10/1914 | France | 401/134 |
| 842965 | 8/1960 | United Kingdom | 604/2 |

Primary Examiner—Steven A. Bratlie
Attorney, Agent, or Firm—Nies, Webner, Kurz & Bergert

[57] ABSTRACT

A disposable, individually packaged, self-contained topical application swab is disclosed. Liquid is initially stored in the swab and then caused to saturate the absorbent end of the swab immediately prior to application, thus eliminating spills and waste. The swab includes an absorbent material such as cotton, gauze, sponge, or the like attached to one end of a hollow plastic tube of small diameter which is sealed on the same end of the tube and which is sealed on the opposite end by a rubber cap. The unit is then inserted into a thin plastic tube of the same diameter as the absorbent material used on the swab to assure correct positioning of the swab. This exterior tube is sealed on one end by a plug containing a fixed lance. The other end of the exterior tube is sealed by the rubber cap on the swab when the swab is inserted into the tube. The entire unit may then be sterilized and strip packaged.

7 Claims, 1 Drawing Sheet

SWAB APPLICATOR

BACKGROUND AND SUMMARY OF THE INVENTION

The present invention provides a disposable, individually packaged, self-contained topical applicatin swab in which the desired liquid is initially stored and then caused to saturate the absorbent end of the swab immediately prior to applicaton, thus eliminating spills, waste and the mess of other topical liquid application systems. The swab of the present invention has medical and household as well as industrial applications.

The swab includes an absorbent material such as cotton, gauze, sponge, or the like attached to one end of a hollow plastic tube of small diameter which is sealed on the same end of the tube and which is sealed on the opposite end by a rubber cap. The unit is then inserted into a thin plastic tube of the same diameter as the absorbent material used on the swab to assure correct positioning of the swab. This exterior tube is sealed on one end by a plug containing a fixed lance. The other end of the exterior tube is sealed by the rubber cap on the swab when the swab is inserted into the tube. The entire unit may then be sterilized and strip packaged.

To use the swab, it is removed from the strip package and the entire swab is depressed by pressing the rubber cap. This action allows the fixed lance in the end of the external tube to rupture the thin seal in the absorbent end of the swab. Next, the swab is removed from the exterior tube by gently pulling the rubber cap of the swab. The swab is then held, preferably in a vertical position with the absorbent end down and the rubber cap is removed from the swab tube. This allows the liquid contained in the stem of the swab to saturate the absorbent material at the end of the swab. The swab is now ready for application. All measurements of the swab are variable depending on the intended use.

DESCRIPTION OF THE PREFERRED EMBODIMENTS

Figure 2:
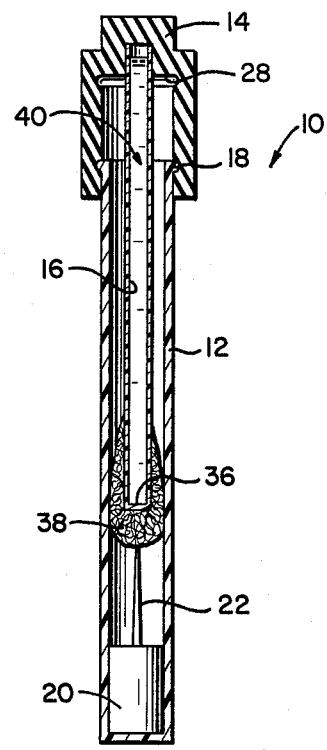
FIG. 2 is a sectional view of the device of FIG. 1 showing the exterior tube seated in the cap and spaced from the inner end of the cap.
Figure 1:
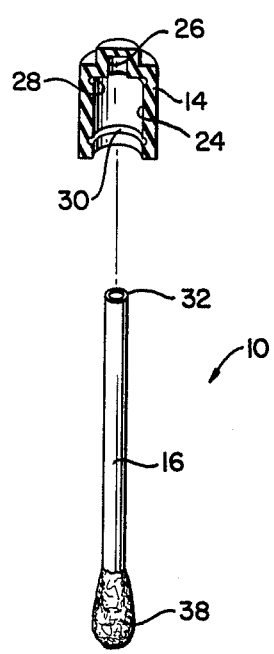
FIG. 1 is an exploded sectional view of the swab applicator of the present invention showing the various components.

In the embodiment of the invention as shown in FIGS. 1 through 5, there is provided a swab applicator 10 which includes exterior tube 12, end cap 14 and inner swab tube 16. The exterior tube, formed of plastic or similar material, is provided with a reinforced rib or bead portion 18 around the circumference of one end thereof and with a plug 20 which seals the other end of the tube 12. A pointed lance 22 is secured to the plug 20 and arranged so as to coincide with the longitudinal axis of the tube 12.

The end cap member 14, formed of rubber or other resilient material, has a main interior bore or channel 24 for receiving the open end of tube 12 and a second interior bore 26 of reduced diameter relative to the main bore 24. The second bore 26 is located axially inwardly of the main bore 24 and is positioned to receive the open end of the swab tube 16.

The end cap 14 has suitable indentations 28, 30 formed in the interior surface of the cap 14 adjacent the main bore 24 for the purpose of receiving the ribbed end 18 of the exterior tube 12. One indented portion 28 is provided at the inner end of the bore 24 and another indented portion 30 is axially spaced from the inner end of the bore 24 so as to be positioned adjacent the open end of the cap 14.

The swab tube 16, containing the desired liquid 40 to be applied, is open at one end 32 and has the other end 34 sealed by a thin plastic film or other suitable cover 36 which may be easily penetrated by the lance 22. An absorbent material 38 such as cotton, gauze of the like is secured to the end 34 of the tube 16 in any suitable manner. The lateral dimension of the absorbent material 38 should be approximately equal to the inner diameter of tube 12 to assist in proper central positioning of the swab 16 within the tube 12. Both tube 12 and tube 16 may be formed of clear plastic or other suitable material.

Figure 3:
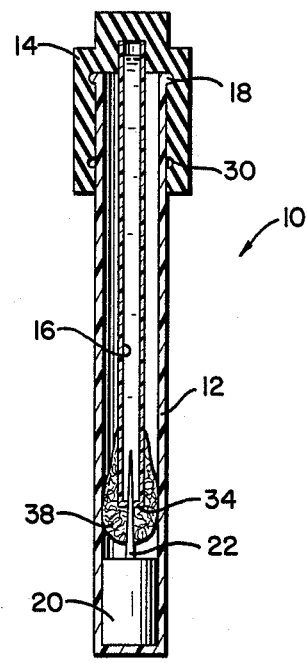
FIG. 3 is sectional view showing the device of FIG. 2 with the cap having been depressed over the exterior tube.

The axial spacing between indentations 28,30 of the end cap 14 and the length and position of the lance 22 should preferably be such as to allow the lance 22 to just touch the absorbent material 38 when the tube 12 is initially installed in the end cap 14, as shown in FIG. 2, while allowing the lance 22 to penetrate firmly through the seal 36 at the lower end 34 of tube 16 when the end cap 14 is pressed down over the exterior tube 12, as shown in FIG. 3.

Figure 4:
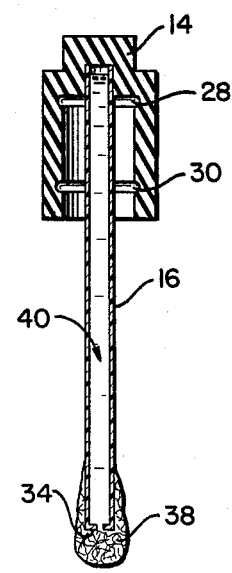
FIG. 4 is a sectional view showing the cap and inner swab with the exterior tube having been removed.
Figure 5:
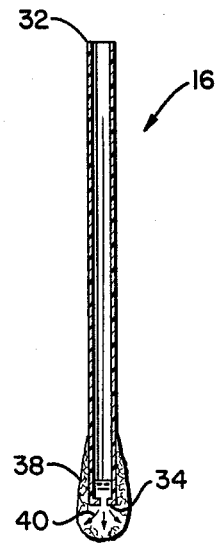
FIG. 5 shows the swab with the cap removed.

Upon removal of the exterior tube 12 with attached lance 22, the swab tube 16 may be held in a vertical position with the absorbent end down, as shown in FIG. 4. The end cap 14 is then removed, allowing the liquid 40 within the tube 16 to pass through the opening in tube end 34 created by the lance 22, thus saturating the absorbent material 38 and providing a swab 16 which is ready for use, as shown in FIG. 5.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A disposable, individually packaged, self contained swab applicator which comprises: a first elongated tubular member having an absorbent material attached at one end thereof, said first tubular member having a sealed end portion at the end to which said absorbent material is attached, a cap member formed of a resilient material and releasably secured to the other end of said first tubular member, said cap member acting to initially seal said other end of said first tubular member; a second elongated tubular member substantially enclosing said first tubular member, said second tubular member having a closed end portion and an open end portion, said closed end portion being located at the end of said applicator opposite the end at which said cap member is located and having a fixed lance secured thereto and extending inwardly of the second tubular member along the longitudinal axis thereof for use in rupturing the sealed end portion of said first tubular member, said open end portion of said second tubular member being releasably secured within said cap member and movable between first and second axial positions within the interior of said cap member upon the application of force in a direction parallel to the longitudinal axes of said first and second tubular members, whereby said lance is moved to rupture the sealed end portion of said first tubular member, said cap member having a main interior bore or channel in which said second tubular member is releasably secured and with a second interior bore of reduced diameter relative to said main bore in which said first tubular member is releasably secured, said second interior bore extending axially outwardly of said main interior bore and with said other end of said first tubular member extending axially outwardly of said main interior bore and within said second interior bore, so that a seal is provided between said other end of said first tubular member and said cap member even after removal of said second tubular member from said cap member and whereby said cap member can be removed from said first tubular member for use of said applicator.

2. The applicator of claim 1 wherein said second tubular member has a diameter approximately equal to that of said absorbent material.

3. The applicator of claim 1 wherein the open end of said second tubular member is provided with a reinforced rib or bead portion.

4. The applicator of claim 3 wherein the interior of said cap member adjacent said channel is provided with an indentation for receiving said bead portion.

5. The applicator of claim 4 wherein the interior of said cap member is provided with a pair of said indentations, the axial spacing between indentations being such that, upon movement of said cap member relative to said second tubular member sufficient to cause said open end of the second tubular member to move from one indentation to the other, said lance is caused to move from a first position exterior to said first tubular member to a second position wherein the lance has penetrated the sealed end portion of said first tubular member to which the absorbent material is attached.

6. The applicator of claim 5, further including a liquid material contained within said first tubular member.

7. The applicator of claim 1 further including a liquid material contained within said first tubular member.

* * * * *